United States Patent
Loverich et al.

(10) Patent No.: US 8,698,329 B2
(45) Date of Patent: Apr. 15, 2014

(54) APPARATUSES AND METHODS FOR USING ENERGY HARVESTING FOR VARIABLE SHOCK ABSORPTION IN A PROSTHETIC DEVICE

(75) Inventors: Jacob J. Loverich, State College, PA (US); David R. Kraige, State College, PA (US); Jeremy E. Frank, Pine Grove Mills, PA (US); Richard T. Geiger, Boalsburg, PA (US)

(73) Assignee: KCF Technologies, Inc., State College, PA (US)

( * ) Notice: Subject to any disclaimer, the term of this patent is extended or adjusted under 35 U.S.C. 154(b) by 0 days.

(21) Appl. No.: 13/481,770

(22) Filed: May 25, 2012

(65) Prior Publication Data

US 2013/0317626 A1    Nov. 28, 2013

(51) Int. Cl.
*F02B 63/04* (2006.01)
*F03G 7/08* (2006.01)
*H02K 7/18* (2006.01)

(52) U.S. Cl.
USPC ......................................................... 290/1 R

(58) Field of Classification Search
USPC ......................................................... 290/1 R
See application file for complete search history.

(56) References Cited

U.S. PATENT DOCUMENTS

| | | | |
|---|---|---|---|
| 4,065,815 A | 1/1978 | Sen-Jung | |
| 4,595,179 A | 6/1986 | Glabiszewski | |
| 5,948,021 A | 9/1999 | Radcliffe | |
| 6,295,914 B1 | 10/2001 | Iversen | |
| 6,517,585 B1 | 2/2003 | Zahedi et al. | |
| 6,610,101 B2 | 8/2003 | Herr et al. | |
| 6,740,125 B2 | 5/2004 | Mosler | |
| 7,066,964 B2 | 6/2006 | Wild | |
| RE39,961 E | 12/2007 | Petrofsky et al. | |
| 7,485,152 B2 | 2/2009 | Haynes et al. | |
| 7,544,214 B2 | 6/2009 | Gramnas | |
| 7,578,799 B2 | 8/2009 | Thorsteinsson et al. | |
| 7,618,463 B2 | 11/2009 | Oddsson et al. | |
| 7,652,386 B2 * | 1/2010 | Donelan et al. | 290/1 R |
| 7,659,636 B2 | 2/2010 | Donelan et al. | |
| 7,883,548 B2 | 2/2011 | Lang | |
| 7,985,265 B2 | 7/2011 | Moser et al. | |
| 2009/0192619 A1 | 7/2009 | Martin et al. | |
| 2010/0023133 A1 | 1/2010 | Fairbanks et al. | |

FOREIGN PATENT DOCUMENTS

DE    10 2008 045 113 A1    3/2010

OTHER PUBLICATIONS

International Search Report dated Sep. 5, 2013, issued in counterpart International Application No. PCT/US2013/042879.

* cited by examiner

*Primary Examiner* — Javaid Nasri
(74) *Attorney, Agent, or Firm* — Novak Druce Connolly Bove + Quigg LLP

(57) ABSTRACT

An apparatus for harvesting energy from motion of a prosthetic limb, wherein the prosthetic limb has motion in at least one degree of freedom, may include a piston configured to receive an input motion and provide an output motion when a first motion in a degree of freedom of the prosthetic limb causes pressure and motion of hydraulic fluid. The apparatus may include an electromagnetic motor for converting mechanical energy of the output motion into corresponding electrical energy delivered to an electrical load and a variable-impedance energy harvesting circuit across terminals of the motor.

25 Claims, 4 Drawing Sheets

APPARATUSES AND METHODS FOR USING ENERGY HARVESTING FOR VARIABLE SHOCK ABSORPTION IN A PROSTHETIC DEVICE

GOVERNMENT LICENSE RIGHTS

This invention was made with government support under Contract No. W81XWH-10-C-0192 awarded by the U.S. Army TATRC (U.S. Army Medical Research Acquisition Activity, 820 Chandler St., Fort Detrick, Md. 21702-5014). The government has certain rights in the invention.

CROSS-REFERENCE TO RELATED APPLICATION

The present disclosure is related to copending U.S. patent application Ser. No. 13/481,769, filed on May 25, 2012, pending, the disclosure of which is incorporated herein by reference.

TECHNICAL FIELD

The present disclosure relates generally to apparatuses and methods for harvesting energy from prosthetic limbs and, more particularly, to apparatuses and methods for using energy harvesting for variable shock absorption in a prosthetic device.

BACKGROUND

The field of prosthetic devices has advanced greatly through the years. Many current lower-limb prosthetics use sensors, microprocessor controllers, and valves or other actuators to assist the user's gait motion, frequently through the use of a hydraulic piston system which facilitates one or more degrees of freedom of motion within the limb, e.g. a knee joint or ankle joint. The ideal amount of damping in a joint is not a fixed value for all patients, or even for all activities for one patient. For an instance, a heavier or more active patient may want more damping in a joint to provide the resistance they need for walking or running, while that high damping value may provide too much motion resistance for a lighter patient. Similarly, a particular patient may want to feel a high damping or stiffness value while walking for comfort and stability, but may want a very low damping value during an activity like bicycling to allow free range of motion of their joints. On an even shorter time scale, as a patient walks over uneven ground or transitions from flat ground to steps, etc., it may be advantageous to vary the damping characteristic of the limb from one step to the next.

Currently many prosthetics use a manually-adjusted hydraulic valve to adjust the flow rate of hydraulic fluid in a piston at the joint. This allows the user or prosthetist the capability to adjust the damping value of the prosthetic, but it is a relatively time-consuming process and requires manually turning a valve with a tool. Thus it is practical for addressing the patient-to-patient variability, but not the activity-to-activity or step-to-step variation.

Some other prosthetic devices use microprocessors and actuators to adjust the resistance valves on a step-by-step basis. This is an obvious improvement over the manually-turned device because adjustments can be made more frequently and can be controlled by software on the limb rather than requiring input by the user or a prosthetist. However, these systems require battery energy to drive the microprocessor and actuators, and thus have a limited life before the user must recharge or change their limb's battery.

Damping is the process of removing mechanical energy from a system. In the above systems this is done by heating up the hydraulic fluid as it is forced through a small orifice valve, and this energy is lost as waste heat. By adding energy harvesting to the limb and converting the mechanical energy into electrical energy which can be stored back in the limb's battery, the same goal of removing mechanical energy is accomplished in a constructive manner instead of a wasteful manner.

What is currently lacking in the art is a method for causing damping by diverting energy into a useful storage reservoir, rather than rejecting that energy to the surrounding environment. By adding energy harvesting and an intelligent control circuit to the limb and converting the mechanical energy of motion into electrical energy which can be stored back in the limb's onboard battery, the same goal of removing mechanical energy is accomplished in a constructive manner instead of a wasteful manner. The addition of an energy harvester increases the functionality of the limb by allowing automatic on-the-fly adjustment of the damping characteristics of the limb. By adding this energy harvesting capability it also is possible to partially or fully recharge the existing battery during use. This can greatly extend the time interval between complete recharges reducing the user's need to replace the battery or to plug the device in to recharge the battery. Indeed, if enough energy is harvested, it would not be necessary to recharge at all.

SUMMARY OF THE INVENTION

In one aspect the disclosure includes an apparatus for harvesting energy from motion of a prosthetic limb, wherein the prosthetic limb has motion in at least one degree of freedom. The apparatus may include a piston configured to receive an input motion and provide an output motion when a first motion in a degree of freedom of the prosthetic limb causes pressure and motion of hydraulic fluid, an electromagnetic motor for converting mechanical energy of the output motion into corresponding electrical energy delivered to an electrical load, and a variable-impedance energy harvesting circuit across terminals of the motor.

In another aspect, the disclosure includes a prosthetic limb comprising a hydraulic cylinder and an energy harvester operably coupled with the hydraulic cylinder. The hydraulic cylinder includes hydraulic fluid and a piston slidably movable in the hydraulic cylinder in response to motion in a degree of freedom of the prosthetic limb. The energy harvester is configured to provide an output motion when a first motion in a degree of freedom of the prosthetic limb causes pressure and motion of hydraulic fluid. The prosthetic limb further includes an electromagnetic motor for converting mechanical energy of said output motion into corresponding electrical energy delivered to an electrical load and/or an energy storage reservoir. The prosthetic limb includes a variable-impedance energy harvesting circuit across terminals of the motor and an energy storage reservoir. The generator is electrically coupled to the energy storage reservoir to direct energy harvested from the input force of the wearer to the energy storage reservoir during use.

In another aspect, the disclosure includes a method of harvesting energy in a prosthetic limb. The method includes moving a prosthetic limb in a degree of freedom, slidably moving a piston in a hydraulic cylinder, in response to said movement of the prosthetic limb in the degree of freedom, to pressurize and move hydraulic fluid in said cylinder and provide an output motion, and directing an output force associated with the output motion to an electromagnetic motor. The method includes converting mechanical energy of the output force into corresponding electrical energy delivered to an electrical load, and varying impedance across terminals of the electromagnetic motor, whereby mechanical energy of the output motion is converted into corresponding electrical energy and delivered to at least one of an electrical load and an energy storage reservoir.

DETAILED DESCRIPTION

Reference will now be made in detail to specific embodiments or features, examples of which are illustrated in the accompanying drawings. Generally, corresponding or similar reference numbers will be used, when possible, throughout the drawings to refer to the same or corresponding parts.

Figure 1:
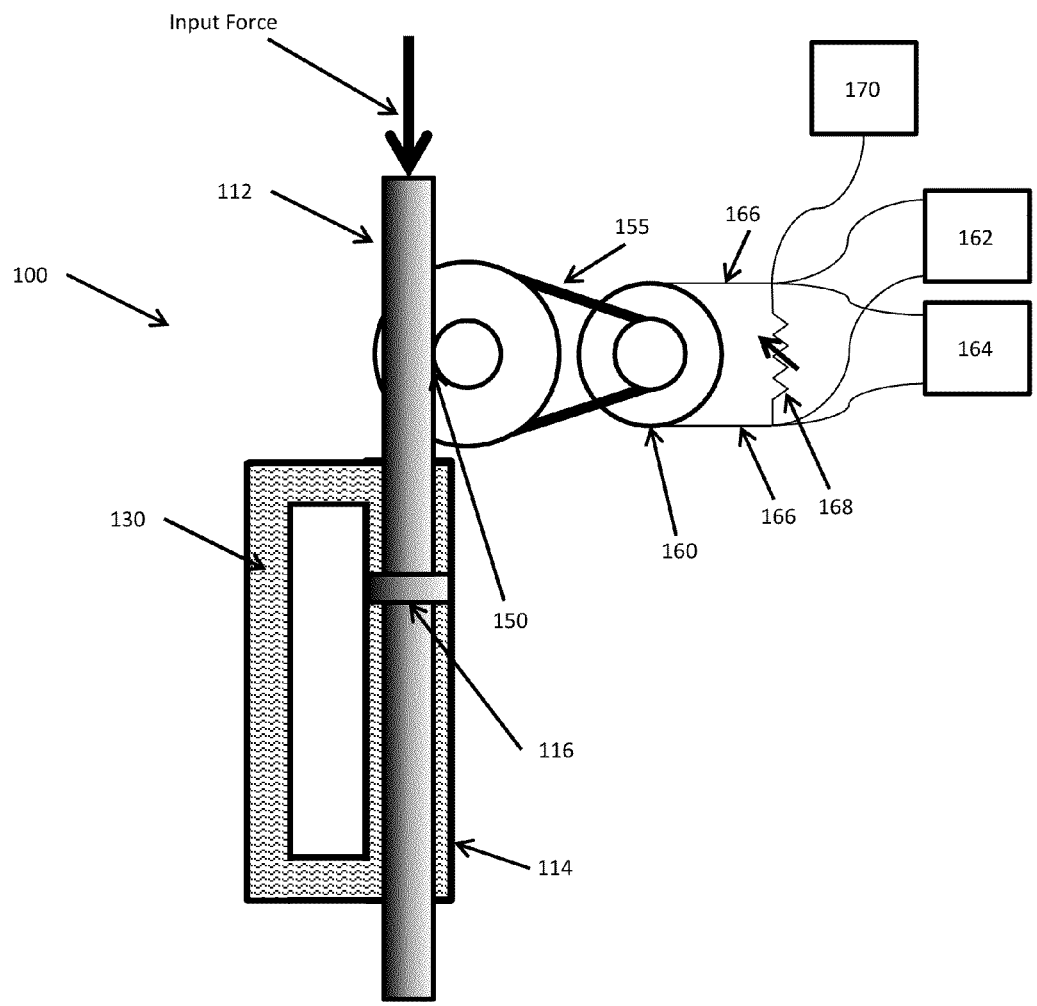
FIG. 1 illustrates an exemplary embodiment of an apparatus for harvesting energy from motion of a prosthetic limb in accordance with various aspects of the disclosure.

Referring now to FIG. 1, an exemplary embodiment of an apparatus 100 for harvesting energy from motion of a prosthetic limb is illustrated. As would be appreciated by persons skilled in the art, the prosthetic limb has motion in at least one degree of freedom. In the embodiment illustrated, the apparatus 100 includes a mechanical arrangement 150 configured to direct output motion and associated output force to a generator 160.

According to various aspects, the apparatus 100 includes an input member 112. The input member 112 may include a hydraulic cylinder 114 and a piston 116 slideable in the hydraulic cylinder 114. The piston 116 is slidably movable in the hydraulic cylinder 114 between a first position and a second position. The piston 116 is configured to receive an input force and an associated input motion generated when a wearer of the prosthetic transfers weight to the limb, which results in an output motion and an associated output force by the piston 116.

As shown in FIG. 1, the apparatus 100 may be a closed hydraulic system. That is, the hydraulic cylinder 114 may be fluidly coupled to both sides of the piston 116 via hydraulic working fluid 130 that is essentially incompressible and cannot change volume.

The generator 160 is coupled with the piston 116 via the mechanical arrangement 150 such that output motion and associated output force from the piston 116 is directed to the generator 160. According to various aspects, if the generator is a linear motor, the mechanical arrangement 150 may include a direct connection between the second piston 136 and the linear motor. If the generator 160 is a rotary motor, the mechanical arrangement may include a rack-and-pinion arrangement or friction wheel connection between the piston 116 and the rotary motor. In any case, the generator 160 is configured to convert mechanical energy of the motion of the piston 116 into corresponding electrical energy, which may be directed to an electrical load 162 and/or an electrical storage reservoir 164 electrically coupled with the generator 160. For example, the electrical storage reservoir may include a rechargeable battery. The generator 160 may be electrically coupled to the rechargeable battery to recharge the battery with energy harvested from input motion applied to the input member 112 of the apparatus 100 by a wearer of the prosthetic during use.

According to various aspects, the electrical load 162 may include a microprocessor control circuit, an electric motor for operating a valve or other actuator, or an electric motor for adjusting the motion of or providing propulsive power to the limb. According to various aspects, the electrical storage reservoir may include a rechargeable battery, a capacitor, or other energy storage device, coupled with a circuit designed to condition the power coming from the generator 160 to be provided as an input to the storage reservoir 164.

It should be appreciated that in some aspects the motion of the piston 116 may be further amplified by an additional set of motion amplification stages, which would gear up the speed input to the generator 160. Such amplification can be accomplished, for example, by taking output motion of a rack-and-pinion arrangement 150 coupled with the piston 116 and amplifying this output motion through a quiet timing belt-and-pulley arrangement 155 or other equivalent mechanism, as would be understood by persons skilled in the art. According to various aspects, the generator 160 may include an electromagnetic motor having a generator mode.

As shown in FIG. 1, the generator 160 may include terminals 166 across which a variable-impedance energy harvesting circuit 168 may extend. The variable-impedance energy harvesting circuit 168 may be operable to vary the deflection and feel of a prosthetic limb by acting as a variable damper. For example, when higher impedance (resistance) is applied across the terminals 166, the motor is able to turn more easily, and when a lower resistance is applied across the terminals 166, the motor is more difficult to turn. Thus, with the higher resistance across the terminals 166, the prosthetic limb will be more free to deflect and will feel softer to the wearer. On the other hand, with the lower resistance across the terminals 166, the limb will be more resistant to deflection and will feel stiffer to the wearer. The apparatus may include a controller 170, such as, for example a microprocessor, configured to control the amount of energy being harvested within a particular step by varying the impedance of the energy harvesting circuit 168. The more energy harvested from a step translates to the limb feeling less "springy," while less energy harvested from of a step leaves more potential energy stored in the spring components of the prosthetic to spring the user forward on a step.

It should be appreciated that the controller 170 may not only be operable to vary the amount of energy harvested per step, for example, during a first step versus a second or subsequent step, but the controller 170 may also be operable to vary the rate of energy harvested during the course of a single step. For example, the controller 170 may be configured to harvest energy out of a step quickly (i.e., at the beginning of a step) so as to provide high stiffness on the initial landing for stability. The controller 170 may be configured to slow the rate of energy harvesting later in the course of that same step so as to soften the landing as the user puts more weight on the limb, thus permitting more travel/cushioning.

Referring again to FIG. 1, since the use of a prosthetic knee or ankle requires the wearer to provide bi-directional forces in a degree of freedom, hydraulic working fluid may be provided on both sides of the piston 116 in a closed hydraulic system. Therefore, force and motion in a first direction of the degree of freedom will cause movement of the piston 116 from a first position toward a second position, while force and motion in a second direction, opposite to the first direction, will cause the piston 116 to return toward the first position. Therefore, energy can be harvested from the amplifier in either one or both directions of travel of the piston 116.

Alternatively, the apparatus 100 may be used in a unidirectional prosthetic such as, for example, a pylon of a shin prosthetic. In such an embodiment, the harvesting apparatus 100 may include a return spring configured to return the piston 116 to their respective neutral positions during the swing phase of a user's stride so that the apparatus 100 is ready to operate again on the user's next step. An example of a return spring is discussed below in connection with the embodiment of FIG. 2. The return spring is required for prosthetic devices that only achieve an incomplete motion cycle from the user input. In either case, energy may be harvested during this return motion as well as the initial motion.

Figure 2:
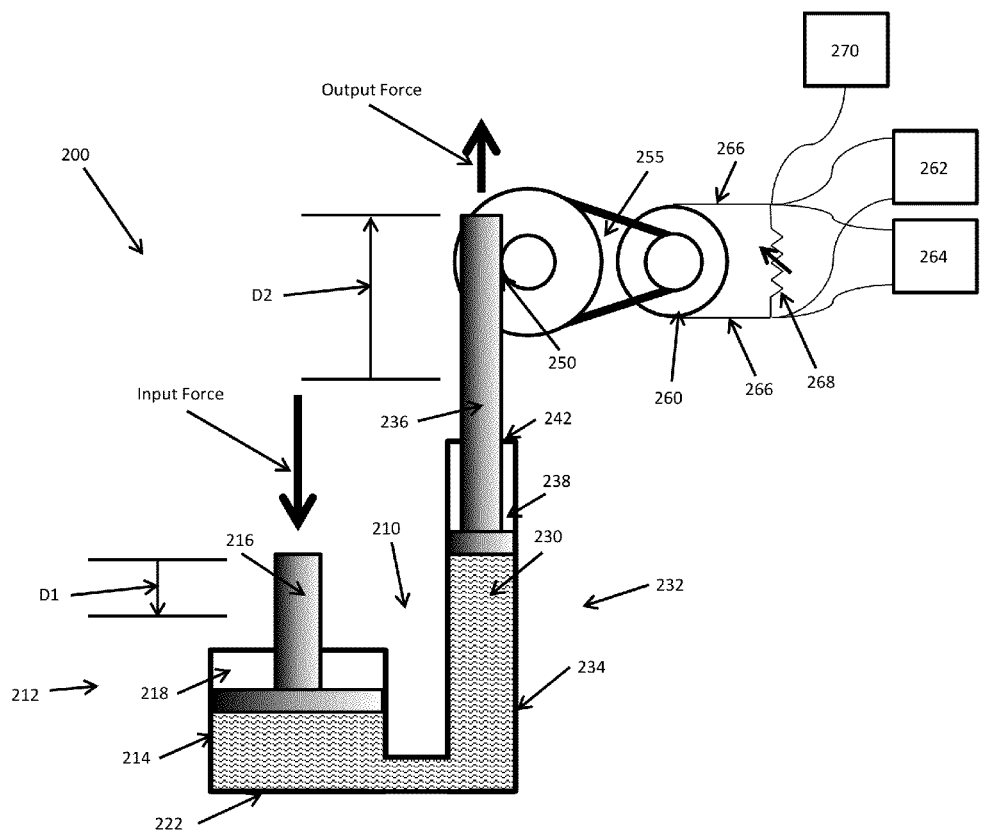
FIG. 2 illustrates an exemplary embodiment of an apparatus for harvesting energy from motion of a prosthetic limb in accordance with various aspects of the disclosure.

Referring now to FIG. 2, an exemplary embodiment of an apparatus 200 for harvesting energy from motion of a prosthetic limb is illustrated. As would be appreciated by persons skilled in the art, the prosthetic limb has motion in at least one degree of freedom. In the embodiment illustrated, the apparatus 200 includes an optional hydraulic amplifier 210 and a mechanical arrangement 250 configured to couple output motion and associated output force of the hydraulic amplifier 210 to a generator 260.

According to various aspects, the hydraulic amplifier 210 includes an input member 212 and an output member 232. The input member 212 may include a first hydraulic cylinder 214 and a first piston 216 slideable in the first hydraulic cylinder 214. The first piston 216 is slidably movable in the first hydraulic cylinder 214 between a first position and a second position. The first piston 216 is configured to receive an input force and an associated input motion generated when a wearer of the prosthetic transfers weight to the limb.

The output member 232 may include a second hydraulic cylinder 234 and a second piston 236 slideable in the second hydraulic cylinder 234. The second piston 236 is slidably movable in the second hydraulic cylinder 234 between a first position and a second position. The second piston 236 is configured to direct the output motion to the generator 260.

As shown in FIG. 2, the hydraulic amplifier 210 may be a closed hydraulic system. That is, the first and second hydraulic cylinders 214, 234 may be fluidly coupled via hydraulic working fluid 230 in the amplifier 210 that is essentially incompressible and cannot change volume.

According to various aspects, the first piston 216 has a face area larger than the face area of the second piston 236. For example, the area of the first piston 216 may be 2-10 times greater than the diameter of the second piston 236. However, it should be appreciated that any desired ratio between the areas of the first and second pistons may be implemented according to the disclosure. As a result, when the first piston 216 receives an input force that slidably moves the first piston a first distance D1, the second piston is displaced a proportionately greater second distance D2. Thus, the hydraulic amplifier 210 amplifies the input motion of the first piston 216 to a greater output motion of the second piston 236.

As persons skilled in the art would understand, because the two pistons and cylinders 214, 216, 234, 236 are designed with different diameters, any given input force and motion to the piston 216, 236 of one of the cylinders 214, 234, results in a force and motion output at the other cylinder which is governed by the ratio of the two piston surface areas. In other words, by making the first piston 216 and first cylinder 214 larger than the second piston 236 and second cylinder 234, the second piston 236 is forced to move farther, while the output force available at the second piston 236 is reduced. For example, if the ratio of areas is 2:1, the second piston 236 will move twice as far the first piston 216, but due to conservation of energy, the output force available at the second piston 236 will be only half as much, minus some amount lost due to the inefficiencies in the system (e.g., hydraulic fluid heating up, friction at the seals, cylinders/hoses/fittings expanding under pressure, etc.).

The generator 260 is coupled with the output member 232 of the hydraulic amplifier 210 via a mechanical arrangement 250. According to various aspects, if the generator is a linear motor, the mechanical arrangement 250 may include a direct connection between the second piston 236 and the linear motor. If the generator 260 is a rotary motor, the mechanical arrangement may include a rack-and-pinion arrangement or friction wheel connection between the second piston 236 and the rotary motor. In any case, the generator 260 is configured to convert mechanical energy of the output motion of the second piston 236 into corresponding electrical energy, which may be directed to an electrical load 262 and/or an electrical storage reservoir 264 electrically coupled with the generator 260. For example, the electrical storage reservoir may include a rechargeable battery. The generator 260 may be electrically coupled to the rechargeable battery to recharge the battery with energy harvested from input motion applied to the input member 212 of the apparatus 200 by a wearer of the prosthetic during use.

According to various aspects, the electrical load 262 may include a microprocessor control circuit, an electric motor for operating a valve or other actuator, or an electric motor for adjusting the motion of or providing propulsive power to the limb. According to various aspects, the electrical storage reservoir may include a rechargeable battery, a capacitor, or other energy storage device, coupled with a circuit designed to condition the power coming from the generator 260 to be provided as an input to the storage reservoir 264.

As shown in FIG. 2, the generator 260 may include terminals 266 across which a variable-impedance energy harvesting circuit 268 may extend. The variable-impedance energy harvesting circuit 268 may be operable to vary the deflection and feel of a prosthetic limb by acting as a variable damper. For example, when higher impedance (resistance) is applied across the terminals 266, the motor is able to turn more easily, and when a lower resistance is applied across the terminals 266, the motor is more difficult to turn. Thus, with the higher resistance across the terminals 266, the prosthetic limb will be more free to deflect and will feel softer to the wearer. On the other hand, with the lower resistance across the terminals 266, the limb will be more resistant to deflection and will feel stiffer to the wearer.

The apparatus may include a controller 270, such as, for example a microprocessor, configured to control the amount of energy being harvested within a particular step by varying the impedance of the energy harvesting circuit 268. The more energy harvested from a step translates to the limb feeling less "springy," while less energy harvested from of a step leaves more potential energy stored in the spring components of the prosthetic to spring the user forward on a step.

It should be appreciated that the controller 270 may not only be operable to vary the amount of energy harvested per step, for example, during a first step versus a second or subsequent step, but the controller 270 may also be operable to vary the rate of energy harvested during the course of a single step. For example, the controller 270 may be configured to harvest energy out of a step quickly (i.e., at the beginning of a step) so as to provide high stiffness on the initial landing for stability. The controller 270 may be configured to slow the rate of energy harvesting later in the course of that same step so as to soften the landing as the user puts more weight on the limb, thus permitting more travel/cushioning.

It should be appreciated that in some aspects the output motion of the second piston 236 may be further amplified by an additional set of motion amplification stages, which would gear up the speed input to the generator 260. Such amplification can be accomplished, for example, by taking output motion of a rack-and-pinion arrangement 250 coupled with the second piston 236 and amplifying this output motion through a quiet timing belt-and-pulley arrangement 255 or other equivalent mechanism, as would be understood by persons skilled in the art. According to various aspects, the generator 260 may include an electromagnetic motor having a generator mode.

Referring again to FIG. 2, the harvesting apparatus 200 may include a return spring configured to return the first and second pistons 216, 236 to their respective neutral positions during the swing phase of a user's stride so that the apparatus 200 is ready to operate again on the user's next step. According to various aspects of the disclosure, the first hydraulic cylinder 212 may include a first chamber 218 on the rod-side of the first piston 216. The second hydraulic cylinder 232 may include a second chamber 238 on the rod-side of the second piston 236. The first and second chambers 218, 238 include pre-charge volumes of air, which are used as air springs to force the pistons back to their first positions. For example, as the second piston 236 approaches the top 242 of the second cylinder 232, as viewed in FIG. 1, the air volume in the second chamber 238 above the second piston 236 is compressed creating a spring return force. This spring return force works to push the first and second pistons 216, 236 of the hydraulic amplifier 210 back to their neutral positions. In certain prosthetic devices, forces exerted by the user's motion cause a complete motion cycle. The return spring described here is required for prosthetic devices that only achieve an incomplete motion cycle from the user input. In either case, energy may be harvested during this return motion as well as the initial motion.

The volume of air in the first chamber 218 behind the first piston 116 also contributes to this spring effect by complementing the spring force above the second piston 236. As the user/wearer of the prosthetic provides an input force to the input member 212, the first piston 216 moves toward the bottom 222 of the first cylinder 212 and the volume of the first chamber 218 above the first piston 216 increases, thereby creating a lower pressure (in some situations below atmospheric pressure) n the first chamber 218 which works to pull the first cylinder back to its neutral position. It should be appreciated that both of these contributors to the spring effect can be included or only one or the other can be utilized, depending on the requirements of the application. If only one air spring is needed, one possible embodiment would be to leave the chamber of one of the cylinders open to atmosphere so that the pressure of air space above that piston remained essentially constant (at atmospheric pressure) and does not contribute to the spring effect.

Referring now to FIGS. 3A thru 4B, exemplary embodiments of an apparatus 300 for harvesting energy from motion of a prosthetic knee 302 and an apparatus 400 for harvesting energy from motion of a prosthetic ankle 402 are illustrated. As would be appreciated by persons skilled in the art, the prosthetic knee has motion in at least one degree of freedom. In the embodiment illustrated, the apparatus 300 includes an optional hydraulic amplifier 310 and a mechanical arrangement 350 configured to couple output motion and associated output force of the hydraulic amplifier 310 to a generator 360.

According to various aspects, the hydraulic amplifier 310 includes an input member 312 and an output member 332. The input member 312 may include a first hydraulic cylinder 314 and a first piston 316 slideable in the first hydraulic cylinder 314. The first piston 316 is slidably movable in the first hydraulic cylinder 314 between a first position and a second position. The first piston 316 is configured to receive an input force and an associated input motion generated when a wearer of the prosthetic transfers weight to the limb.

The output member 332 may include a second hydraulic cylinder 334 and a second piston 336 slideable in the second hydraulic cylinder 334. The second piston 336 is slidably movable in the second hydraulic cylinder 334 between a first position and a second position. The second piston 336 is configured to direct the output motion to the generator 360.

Figure 3:
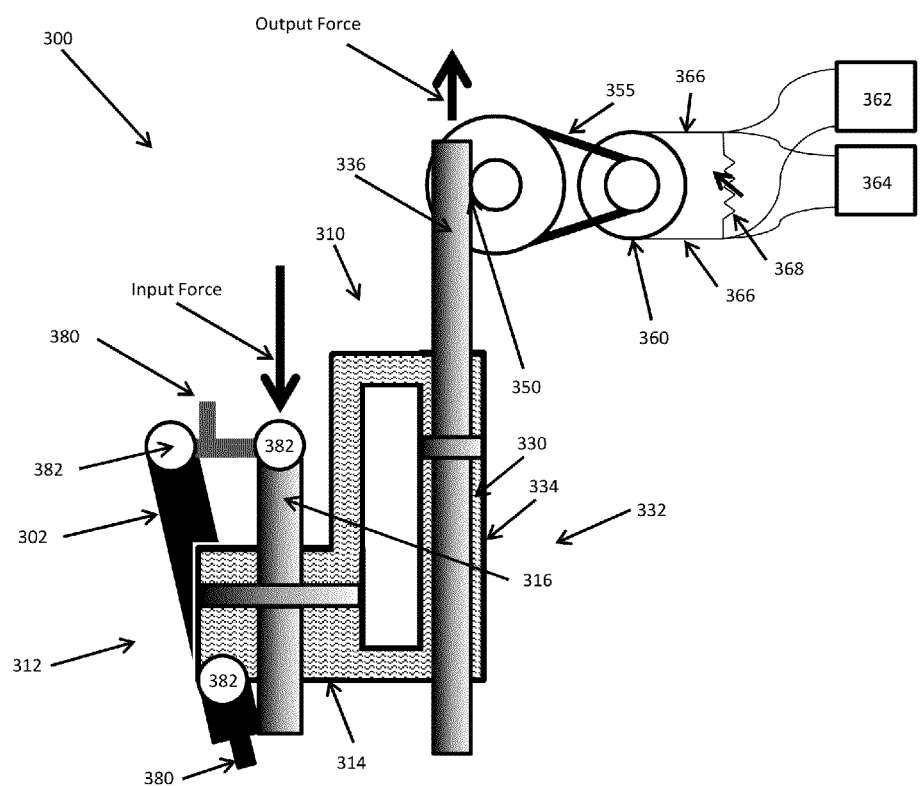
FIG. 3 illustrates an exemplary embodiment of an apparatus for harvesting energy from motion of a prosthetic knee in accordance with various aspects of the disclosure.

As shown in FIG. 3, the hydraulic amplifier 310 may be a closed hydraulic system. That is, the first and second hydraulic cylinders 314, 334 may be fluidly coupled via hydraulic working fluid 330 in the amplifier 310 that is essentially incompressible and cannot change volume.

According to various aspects, the first piston 316 has a face area larger than the face area of the second piston 336. For example, the area of the first piston 316 may be 2-10 times greater than the diameter of the second piston 336. However, it should be appreciated that any desired ratio between the areas of the first and second pistons may be implemented according to the disclosure. As a result, when the first piston 316 receives an input force that slidably moves the first piston a first distance, the second piston is displaced a proportionately greater second distance. Thus, the hydraulic amplifier 310 amplifies the input motion of the first piston 316 to a greater output motion of the second piston 336.

As persons skilled in the art would understand, because the two pistons and cylinders 314, 316, 334, 336 are designed with different diameters, any given input force and motion to the piston 316, 336 of one of the cylinders 314, 334, results in a force and motion output at the other cylinder which is governed by the ratio of the two piston surface areas. In other words, by making the first piston 316 and first cylinder 314 larger than the second piston 336 and second cylinder 334, the second piston 336 is forced to move farther, while the output force available at the second piston 336 is reduced. For example, if the ratio of areas is 2:1, the second piston 336 will move twice as far the first piston 316, but due to conservation of energy, the output force available at the second piston 336 will be only half as much, minus some amount lost due to the inefficiencies in the system (e.g., hydraulic fluid heating up, friction at the seals, cylinders/hoses/fittings expanding under pressure, etc.).

The generator 360 is coupled with the output member 332 of the hydraulic amplifier 310 via a mechanical arrangement 350. According to various aspects, if the generator is a linear motor, the mechanical arrangement 350 may include a direct connection between the second piston 336 and the linear motor. If the generator 360 is a rotary motor, the mechanical arrangement may include a rack-and-pinion arrangement or friction wheel connection between the second piston 336 and the rotary motor. In any case, the generator 360 is configured to convert mechanical energy of the output motion of the second piston 336 into corresponding electrical energy, which may be directed to an electrical load 362 and/or an electrical storage reservoir 364 electrically coupled with the generator 360. For example, the electrical storage reservoir may include a rechargeable battery. The generator 360 may be electrically coupled to the rechargeable battery to recharge the battery with energy harvested from input motion applied to the input member 312 of the apparatus 310 by a wearer of the prosthetic during use.

According to various aspects, the electrical load 362 may include a microprocessor control circuit, an electric motor for operating a valve or other actuator, or an electric motor for adjusting the motion of or providing propulsive power to the limb. According to various aspects, the electrical storage reservoir 364 may include a rechargeable battery, a capacitor, or other energy storage device, coupled with a circuit designed to condition the power coming from the generator 360 to be provided as an input to the storage reservoir.

Figure 4:
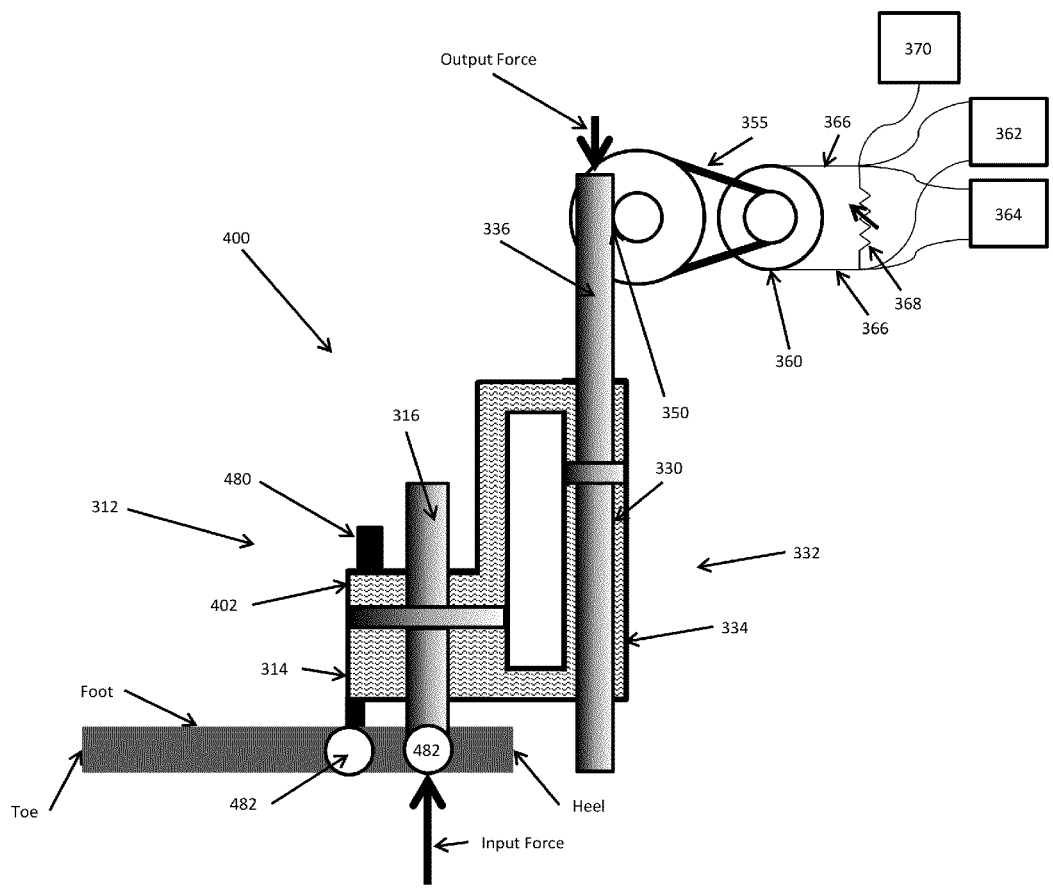
FIG. 4 illustrates an exemplary embodiment of an apparatus for harvesting energy from motion of a prosthetic ankle in accordance with various aspects of the disclosure.

Referring now to FIGS. 3 and 4, the generator 360 may include terminals 366 across which a variable-impedance energy harvesting circuit 368 may extend. The variable-impedance energy harvesting circuit 368 may be operable to vary the deflection and feel of a prosthetic limb by acting as a variable damper. When higher impedance (resistance) is applied across the terminals 366, the motor is able to turn more easily, and when a lower resistance is applied across the terminals 366, the motor is more difficult to turn. Thus, with the higher resistance across the terminals 366, the prosthetic limb will be more free to deflect and will feel softer to the wearer. On the other hand, with the lower resistance across the terminals 366, the limb will be more resistant to deflection and will feel stiffer to the wearer.

The apparatus may include a controller 370, such as, for example a microprocessor, configured to control the amount of energy being harvested within a particular step by varying the impedance of the energy harvesting circuit 368. The more energy harvested from a step translates to the limb feeling less "springy," while less energy harvested from of a step leaves more potential energy stored in the spring components of the prosthetic to spring the user forward on a step.

It should be appreciated that the controller 370 may not only be operable to vary the amount of energy harvested per step, for example, during a first step versus a second or subsequent step, but the controller 370 may also be operable to vary the rate of energy harvested during the course of a single step. For example, the controller 370 may be configured to harvest energy out of a step quickly (i.e., at the beginning of a step) so as to provide high stiffness on the initial landing for stability. The controller 370 may be configured to slow the rate of energy harvesting later in the course of that same step so as to soften the landing as the user puts more weight on the limb, thus permitting more travel/cushioning.

It should be appreciated that in some aspects the output motion of the second piston 336 may be further amplified by an additional set of motion amplification stages, which would gear up the speed input to the generator 360. Such amplification can be accomplished, for example, by taking output motion of a rack-and-pinion arrangement 350 coupled with the second piston 336 and amplifying this output motion through a quiet timing belt-and-pulley arrangement 355 or other equivalent mechanism, as would be understood by persons skilled in the art. According to various aspects, the generator 360 may include an electromagnetic motor having a generator mode.

Since the use of a prosthetic knee or ankle requires the wearer to provide bi-directional forces in a degree of freedom, hydraulic working fluid may be provided on both sides of the first and second pistons 316, 336 in a closed hydraulic system. Therefore, force and motion in a first direction of the degree of freedom will cause movement of the first and second pistons 316, 336 from a first position toward a second position, while force and motion in a second direction, opposite to the first direction, will cause the first and second pistons 316, 336 to return toward the first position. Therefore, energy can be harvested from the amplifier in either one or both directions of travel of the pistons 316, 336.

Referring again to FIGS. 3 and 4, the harvesting apparatus 300 may include a number of attachment points 380 for coupling the apparatus 300 to a prosthetic knee, as a well as a number of pivot points 382 allowing pivotal motion of the harvesting apparatus 300 relative to the prosthetic. Similarly, the harvesting apparatus 400 may include a number of attachment points 480 for coupling the apparatus 400 to a prosthetic ankle, as a well as a number of pivot points 482 allowing pivotal motion of the harvesting apparatus 400 relative to the prosthetic.

It should be appreciated that one or more of the aforementioned embodiments may include additional components including, but not limited to, sensors, microprocessor controllers, valves, and actuators configured to assist the wearer's gait motion. One or more of the embodiments may include a joint member and an arrangement for controlling motion of the joint member. One or more of the embodiments may include an arrangement configured to actively propel the wearer forward. Further, one or more of the aforementioned components and arrangements may be powered by the energy storage reservoir.

In operation, energy may be harvested from a prosthetic limb by moving a prosthetic limb in a degree of freedom, slidably moving a piston in a hydraulic cylinder, in response to the movement of the prosthetic limb in the degree of freedom, to pressurize and move hydraulic fluid in said cylinder, and hydraulically amplifying motion of the piston to a greater output motion. The output motion may be directed to a generator configured to convert mechanical energy of the output motion into corresponding electrical energy and direct the electrical energy to an electrical load and/or an energy storage reservoir.

INDUSTRIAL APPLICABILITY

As mentioned above, only a small amount of deflection is tolerable in a prosthetic limb. This small deflection is not enough to generate an appreciable amount of electrical energy when made available to an electromechanical generator. Simply amplifying the deflection would generate a force that is often too large for the small electromechanical components used in prosthetics and would not rotate an electromechanical generator enough to generate a useful amount of energy. Therefore, a hydraulic amplifier is designed to transform the small amount of tolerable deflection into a large amount of motion for running an electromechanical generator while reducing the amount of force at the output of the amplifier to a force that is more appropriate for the small components capable of being used in prosthetics. This design is then configured to properly match the mechanical impedance of the generator being used to source energy to the storage system.

From the foregoing, it will be appreciated that, although specific embodiments have been described herein for purposes of illustration, various modifications or variations may be made without deviating from the spirit or scope of inventive features claimed herein. Other embodiments will be apparent to those skilled in the art from consideration of the specification and figures and practice of the arrangements disclosed herein. It is intended that the specification and disclosed examples be considered as exemplary only, with a true inventive scope and spirit being indicated by the following claims and their equivalents.

What is claimed is:

1. An apparatus for harvesting energy from motion of a prosthetic limb, the prosthetic limb having motion in at least one degree of freedom, the apparatus comprising:
   a piston configured to receive an input motion and provide an output motion when a first motion in a degree of freedom of the prosthetic limb causes pressure and motion of hydraulic fluid against a surface of said piston;
   an electromagnetic motor for converting mechanical energy of said output motion into corresponding electrical energy delivered to an electrical load; and
   a variable-impedance energy harvesting circuit across terminals of the motor, the circuit being operable to act as a variable damper on said motion of the prosthetic limb.

2. The apparatus of claim 1, wherein variation of resistance across the terminals of the motor varies an amount of a user's walking energy that is harvested as electrical energy.

3. The apparatus of claim 1, wherein variation of resistance across the terminals of the motor varies a damping characteristics of the prosthetic limb.

4. The apparatus of claim 1, wherein the electromagnetic motor has a generator mode.

5. The apparatus of claim 1, wherein the electromagnetic motor comprises one of a rotary motor and a linear motor.

6. The apparatus of claim 1, further comprising a hydraulic amplifier mechanically coupled with the piston and the electromagnetic motor, the hydraulic amplifier being configured to amplify the input motion of the piston such that the output motion is greater than the input motion, the hydraulic amplifier being configured to direct a force associated with the output motion to the electromagnetic motor.

7. The apparatus of claim 6, wherein the hydraulic amplifier comprises:
   the piston slidably movable in a first hydraulic cylinder between a first position and a second position; and
   a second piston slidably movable in a second hydraulic cylinder between a first position and a second position, the second piston including an output member configured to direct the output force to the generator.

8. The apparatus of claim 7, wherein the piston is configured to move a first distance in response to the input motion, the movement of the piston by the first distance causing the second piston to move a second distance, the second distance being greater than the first distance.

9. The apparatus of claim 8, wherein the hydraulic amplifier comprises a closed hydraulic system with essentially incompressible working hydraulic fluid, and the first hydraulic cylinder has a diameter larger than a diameter of the second hydraulic cylinder.

10. The apparatus of claim 7, further comprising a return spring configured to return the piston and the second piston to their respective first positions.

11. The apparatus of claim 7, wherein a second motion in the degree of freedom of the prosthetic limb opposite to said first motion causes pressure and motion of the hydraulic fluid configured to return the piston and the second piston to their respective first positions.

12. The apparatus of claim 1, wherein a higher resistance across the terminals allows the motor to turn more easily, while a lower resistance across the terminals makes the motor more difficult to turn.

13. The apparatus of claim 12, wherein with the higher resistance, the prosthetic limb will be more free to deflect and will feel softer to a wearer, while with the lower resistance, the limb will be more resistant to deflection and will feel stiffer to the wearer.

14. The apparatus of claim 1, wherein resistance across the terminals may be varied at least one of from step-to-step and over the course of a single step.

15. The apparatus of claim 1, further comprising a controller, the controller containing instructions for operation to vary the resistance at least one of from step-to-step and over the course of a single step to vary at least one of the stiffness and shock absorption characteristics of the prosthetic limb.

16. The apparatus of claim 15, wherein the controller is powered by energy harvested by the apparatus.

17. The apparatus of claim 16, wherein the energy is directed from the storage reservoir to the controller.

18. An prosthetic limb, comprising:
   a hydraulic cylinder including hydraulic fluid and a piston slidably movable in the hydraulic cylinder in response to motion in a degree of freedom of the prosthetic limb;
   an energy harvester operably coupled with the hydraulic cylinder, the energy harvester including an output member associated with said piston, the output member being configured to provide an output motion when a first motion in a degree of freedom of the prosthetic limb causes pressure and motion of hydraulic fluid against a surface of said piston, the energy harvester including an electromagnetic motor for converting mechanical energy of said output motion into corresponding electrical energy;
   a variable-impedance energy harvesting circuit across terminals of the motor; and
   an energy storage reservoir, the electromagnetic motor being electrically coupled to the energy storage reservoir to direct energy harvested from said motion of the prosthetic limb to the energy storage reservoir or an electrical load, the circuit being operable to act as a variable damper on said motion of the prosthetic limb.

19. The prosthetic limb of claim 18, further comprising at least one component selected from sensors, microprocessor controllers, valves, and actuators configured to assist gait motion of a wearer of the prosthetic limb, said at least one component being powered by a battery.

20. The prosthetic limb of claim 18, further comprising a joint member and an arrangement for controlling motion of the joint member, the arrangement including at least one component powered by a battery.

21. The prosthetic limb of claim 18, further including an arrangement configured to actively propel the wearer forward, the arrangement including at least one component powered by a battery.

22. The apparatus of claim 18, further comprising a hydraulic amplifier mechanically coupled with the piston and the electromagnetic motor, the hydraulic amplifier being configured to amplify the input motion of the piston such that the output motion is greater than the input motion, the hydraulic amplifier being configured to direct a force associated with the output motion to the electromagnetic motor.

23. The apparatus of claim 22, wherein the hydraulic amplifier comprises:
   the piston slidably movable in a first hydraulic cylinder between a first position and a second position; and
   a second piston slidably movable in a second hydraulic cylinder between a first position and a second position, the second piston including an output member configured to direct the output force to the generator.

24. The apparatus of claim 23, further comprising a return spring configured to return the piston and the second piston to their respective first positions.

25. The apparatus of claim 23, further comprising a torsion resistant arrangement configured to couple the piston to the first hydraulic cylinder such that the piston is prevented from rotating within the first hydraulic cylinder.

* * * * *